United States Patent [19]

Reichert et al.

[11] Patent Number: 5,537,993
[45] Date of Patent: Jul. 23, 1996

[54] GAS RATIO CONTROL DEVICE FOR ANESTESIA APPARATUS

[75] Inventors: Dirk-Stefan Reichert; Götz Kullik, both of Lübeck; Wolfgang Falb, Krummesse; Eckhard Schmudde, Pansdorf; Thorsten Haase, Ratzeburg, all of Germany

[73] Assignee: Drägerwerk AG, Lübeck, Germany

[21] Appl. No.: 524,609

[22] Filed: Sep. 7, 1995

[30] Foreign Application Priority Data

Oct. 18, 1994 [DE] Germany ............... 44 37 207.8

[51] Int. Cl.$^6$ ........................................... A61M 16/12
[52] U.S. Cl. ......................... 128/203.14; 128/203.25
[58] Field of Search ............... 128/203.12, 203.25, 128/203.14, 204.18, 204.21, 204.22, 204.25, 205.11, 205.24

[56] References Cited

U.S. PATENT DOCUMENTS

| | | | |
|---|---|---|---|
| 3,047,210 | 7/1962 | Best ......................... | 73/861.47 X |
| 4,015,617 | 4/1977 | Connolly ................... | 137/88 |
| 4,191,952 | 3/1980 | Schreiber et al. ......... | 340/611 |
| 4,328,823 | 5/1982 | Schreiber .................. | 137/88 |
| 4,442,856 | 4/1984 | Betz .......................... | 137/98 |
| 4,555,952 | 12/1985 | Jenkins ..................... | 73/861.47 |
| 4,972,831 | 11/1990 | von dem Hagen et al. ... | 128/204.21 |
| 5,335,652 | 8/1994 | Falb et al. ................. | 128/203.14 |
| 5,411,019 | 5/1995 | Smith ........................ | 128/203.25 |

FOREIGN PATENT DOCUMENTS

| | | | |
|---|---|---|---|
| 2548908 | 1/1985 | France ...................... | 128/203.12 |
| 3219552A1 | 5/1982 | Germany . | |
| 3810745 | 3/1988 | Germany . | |
| 4111139A1 | 8/1991 | Germany . | |
| 2148721 | 6/1985 | United Kingdom ...... | 128/203.12 |

*Primary Examiner*—Edgar S. Burr
*Assistant Examiner*—Eric P. Raciti
*Attorney, Agent, or Firm*—McGlew and Tuttle

[57] ABSTRACT

A gas ratio control device for anesthesia apparatus, includes an anesthetic gas feed line, which has, in a series-connected arrangement, a control valve with an inlet chamber, an anesthetic gas-adjusting valve and a first measuring resistance, and an oxygen feed line, which has a second measuring resistance, wherein the dynamic pressure received from the measuring resistances is sent to a proportional element, which controls the control valve. A flow-proportional addition of the anesthetic gas is possible even at low oxygen flow rates. This is achieved by the outlet chamber and the first pressure chamber being connected to one another in one piece in terms of flow. The anesthetic gas-adjusting valve is arranged in front of the inlet chamber of the control valve in terms of flow. A flow resistance is provided between two chambers limited by diaphragms of the proportional element.

5 Claims, 3 Drawing Sheets

5,537,993

GAS RATIO CONTROL DEVICE FOR ANESTESIA APPARATUS

FIELD OF THE INVENTION

The present invention pertains to a gas ratio control device for anesthesia apparatus comprising an anesthetic gas feed line, which has, in a series-connected arrangement, a control valve with an inlet chamber and with an outlet chamber, an anesthetic gas-adjusting valve and a first measuring resistance, as well as an oxygen feed line, which has, in a series-connected arrangement, an oxygen-adjusting valve and a second measuring resistance, with a proportional element, which has a first pressure chamber, which receives the dynamic pressure from the first measuring resistance and is limited by a first diaphragm, and a second pressure chamber, which receives the dynamic pressure from the second measuring resistance and is limited by a second diaphragm, a slide, which connects the diaphragms, actuates the control valve and is passed through at least two chambers divided by a projection, whose chamber volume is influenced by the deflection of the diaphragms.

BACKGROUND OF THE INVENTION

A gas ratio control device of this type has become known from DE 41 11 139 A1 (corresponding to U.S. Pat. No. 5,335,652; U.S. Pat. No. 5,335,652 is hereby incorporated by reference). Anesthetic gas, laughing gas in this case, is sent in the prior-art gas ratio control device into an inlet chamber of a control valve via an anesthetic gas feed line, and then to a fresh gas outlet from an outlet chamber of the control vane via an anesthetic gas-adjusting valve and a first measuring resistance. Oxygen is also sent as an additional gas via an oxygen feed line, an oxygen-adjusting valve and a second measuring resistance to the fresh gas outlet, where the two gas flows merge.

Dynamic pressures, which are sent as a differential pressure to a proportional element, are generated by the gas flows at the measuring resistances, and the proportional element controls the control valve in the anesthetic gas feed line according to the value of the difference between the two dynamic pressures so that the anesthetic gas flow, i.e., the flow of laughing gas, does not exceed a certain value in relation to the flow of oxygen.

The proportional element has a first pressure chamber to receive the dynamic pressure generated at the first measuring resistance, and a second pressure chamber to receive the dynamic pressure generated at the second measuring resistance. A diaphragm, which is deflected in proportion to the pressure prevailing in the pressure chambers, is located in each pressure chamber. A ball seat vane in the control valve is actuated via a rod connecting the diaphragms, as a result of which the flow of anesthetic gas from the inlet chamber into the outlet chamber changes.

Difficulties in adjustment arise in the case of forms of anesthesia involving very low flow rates of fresh gas, e.g., an oxygen flow rate of less than 1 L/minute; these difficulties may cause the flow of anesthetic gas through the control vane to be shut off completely or partially, as a result of which the oxygen concentration in the fresh gas may increase up to 100 vol.%. This is due essentially to the fact that the rod leading from the first pressure chamber into the outlet chamber and actuating the ball seat valve must overcome frictional forces at the sealing seat between the first pressure chamber and the outlet chamber. The frictional forces are also increased by the fact that the feed pressure occurring in the anesthetic gas feed line in the worst case may act in the outlet chamber. Since the pressure in the outlet chamber also acts on the sealing seat between the outlet chamber and the first pressure chamber, the frictional force increases as a result. In addition, such diaphragm-controlled valves tend to swing.

A pressure-reducing vane with a closing piston, which is connected to a control piston located in a control cylinder and to a damping piston accommodated in a damping cylinder, has been known from DE 32 19 552 A1. A control pressure actuating the control piston is admitted to the control cylinder. The damping piston divides the damping cylinder into an upper cylinder space and a lower cylinder space, which are connected to one another via a laminar throttle. The sensitivity of the closing piston to suddenly occurring pressure shocks is reduced by the throttled gas exchange between the two cylinder spaces on both sides of the damping cylinder. However, the effectiveness of damping depends on the control pressure actuating the control piston in the prior-an pressure-reducing valve, because the lower cylinder space and the control cylinder are connected to one another via a bypass line. Thus, the pressure equalization via the laminar throttle during the movement of the damping piston is also influenced by the pressure and flow conditions in the bypass line.

To make possible the operation of the prior-an gas ratio control device even at low gas flow rates, attempts were made to bridge over the control valve with a bypass that can be connected (DE-C 38 10 745), but this makes possible only a constant addition of the anesthetic gas to the flow of fresh gas, and the amount added is determined by the throttling point of the bypass line.

SUMMARY AND OBJECTS OF THE INVENTION

The primary object of the present invention is to improve a gas ratio control device such that a flow-proportional addition of the anesthetic gas to the fresh gas is possible even at low oxygen flow rate values.

This object is attained in that the outlet chamber and the first pressure chamber are connected to one another in one piece in terms of flow; that the anesthetic gas-adjusting valve is arranged in front of the inlet chamber in the direction of flow; and that a flow resistance throttling the exchange of gas between the chambers is provided.

The advantage of the present invention is essentially that both opening and closing forces are minimized due to the changed connections of the control valve to the anesthetic gas-adjusting valve in front of the inlet chamber of the control valve and to the elimination of a sealing seat, on the one hand, and that an effective damping of the slide actuating the control valve is achieved by the measuring resistance between the chambers limited by the diaphragms, on the other hand. This damping operates independently from the control pressures deflecting the diaphragms. The measuring resistance may be designed as a throttle bore within the projection, and the slide is passed through the projection with a clearance fit, so that most of the gas exchange takes place via the throttle bore. These measures ensure good response of the proportional element to small differences in pressure between the first and second pressure chambers.

At least one of the chambers is advantageously connected to the environment via an additional flow resistance, so that an exchange of gas between the chamber and the environment is possible. It is also possible for both chambers to be connected to the environment via flow resistances. By adjusting the individual flow resistances, a good response behavior of the proportional element can be set at small pressure differences between the pressure chambers.

The projection between the chambers preferably has a hole accommodating the slide, and the diameter of the hole and the diameter of the slide are selected to be such that a gas-carrying annular gap, which acts as a flow resistance between the chambers, is formed.

The slide advantageously is comprised of a first slide section and a second slide section, wherein the first slide section has two pressing pieces, which are in contact with the diaphragms and are connected to one another via a rod guided in a hole. The second slide section is a plunger, which is displaceable in a clearance fit and actuates the control valve. The diaphragms are made of a flaccid, flexible elastomer and lie displaceably on the pressing pieces. Warping, which may occur between the diaphragms and the slide sections during mounting, is thus avoided, and the friction of the slide sections within the hole or the clearance-fit is further reduced compared with a rigid connection between the slide and the diaphragms.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE DEVICE OF FIG. 1

Figure 1:
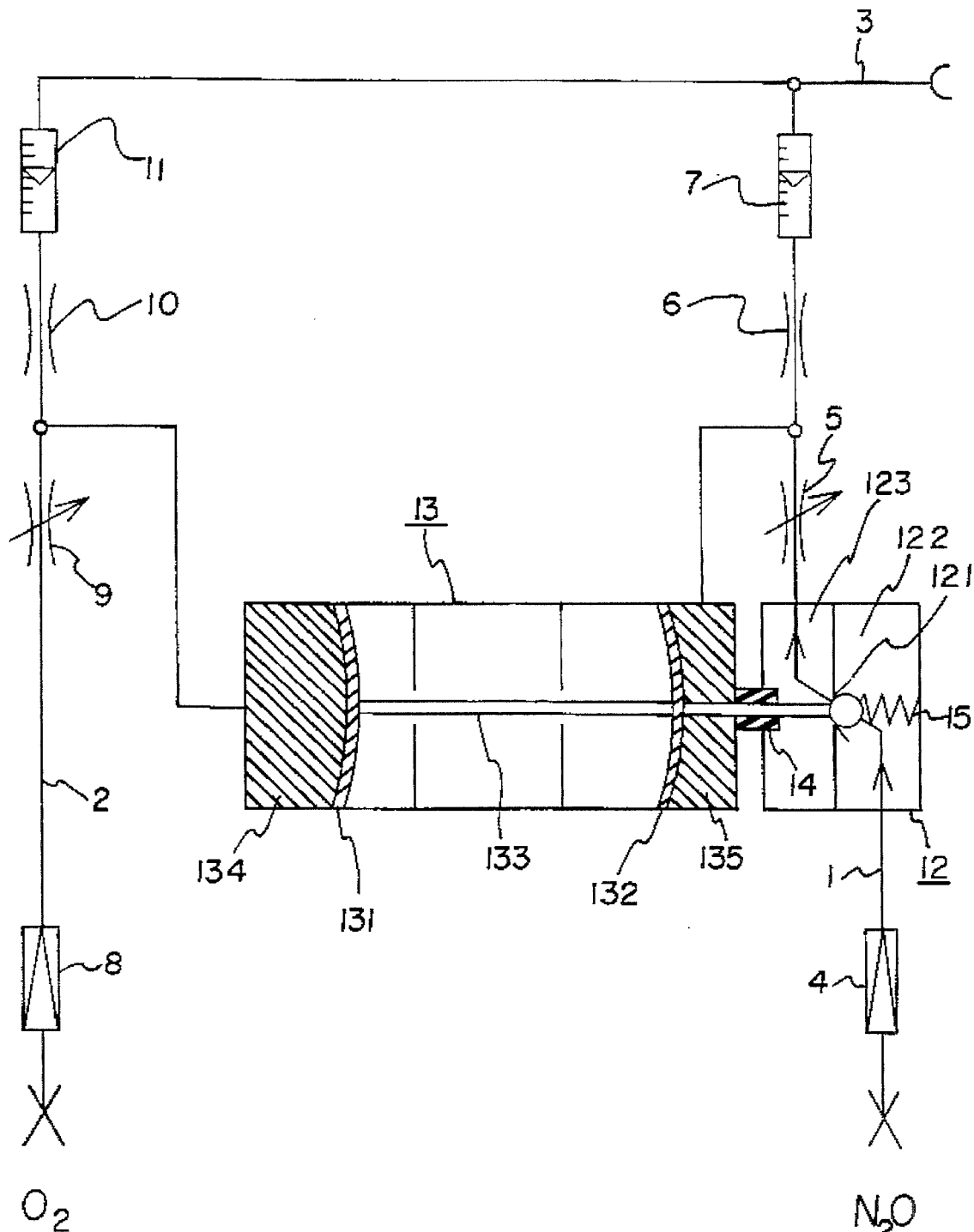
FIG. 1 is a schematic view of a first gas ratio control device according to the state of the art.

In the gas ratio control device according to the state of the art shown in FIG. 1, an anesthetic gas ($N_2O$) feed line 1 and an oxygen feed line 2 are united together in a fresh gas outlet 3. The fresh gas outlet 3 is followed by an anesthetic gas evaporator, which is not shown in FIG. 1. The anesthetic gas feed line 1 contains a first pressure reducer 4, an anesthetic gas-adjusting valve 5, a first measuring resistance 6, as well as a first flow-measuring tube 7. A second pressure reducer 8, an oxygen-adjusting valve 9, a second measuring resistance 10, and a second flow-measuring tube 11 are provided in the same manner in the oxygen feed line 2. A control valve 12, which is actuated via a first proportional element 13, is located in the anesthetic gas feed line 1 between the first pressure reducer 4 and the anesthetic gas-adjusting valve 5. The first proportional element 13 consists of a first diaphragm 132 and a second diaphragm 131, which are connected to one another via a slide 133. The diaphragms 132, 131 limit a first pressure chamber 135, to which an anesthetic gas dynamic pressure picked up (present) in front of the first measuring resistance 6 is admitted, and a second pressure chamber 134, on which an oxygen dynamic pressure picked up (present) in front of the second measuring resistance 10 acts.

Depending on the value of the oxygen dynamic pressure in relation to the anesthetic gas dynamic pressure, the slide 133 is deflected to the right or left. The control valve 12 consists of a spring-loaded ball seat valve 121, which is arranged between an inlet chamber 122 and an outlet chamber 123 and can be opened or closed by the slide 133. The ball of the ball seat valve 121 is pressed into the valve seat by a spring 15 and a pressure difference acting between the inlet chamber 122 and the outlet chamber 123. A sealing seat 14, which prevents both gas from flowing off into the environment and a mutual overflow from occurring between the first pressure chamber 135 and the outlet chamber 123 from occurring, is located at the point of passage of the slide 133 between the first pressure chamber 135 and the outlet chamber 123. To open the ball seat valve 121, the force of the spring 15, the pressing force resulting from the pressure difference between the inlet chamber 122 and the outlet chamber 123, which acts on the ball of the ball seat valve 121, as well as the frictional force caused by the sealing seat 14, must be overcome. Since the sealing seat 14 usually consists of an elastomer, which is deformed under the actually prevailing pressure, the frictional force generally depends on the pressure. The flow of anesthetic gas in the anesthetic gas feed line 1 can be throttled or even shut off completely with the ball seat valve 121. The ball seat valve 121 is, e.g., in the shut-off position when the oxygen dynamic pressure has dropped and the second diaphragm 131 is deflected to the left together with the slide 133. The feed of anesthetic gas is controlled by the interaction between the oxygen dynamic pressure and the anesthetic gas dynamic pressure, and it is ensured that the minimum oxygen concentration cannot drop below, e.g., 25 vol.%.

DETAILED DESCRIPTION OF THE PREFERRED EMBODIMENTS

Figure 2:
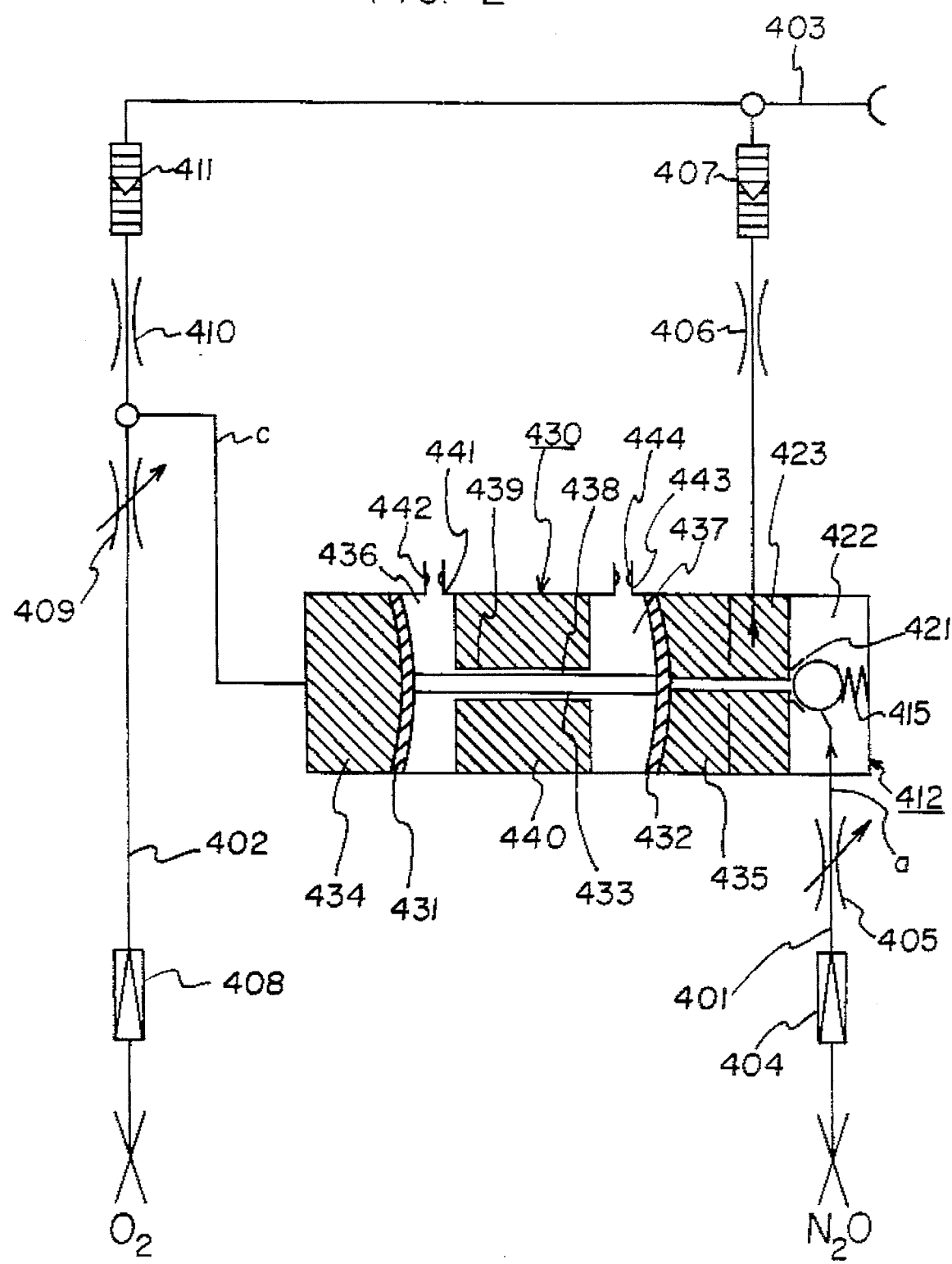
FIG. 2 is a schematic view of a second gas ratio control device according to the present invention.

FIG. 2 shows a gas ratio control device with a second proportional element generally designated 430 according to the present invention. Compared with FIG. 1, the anesthetic gas-adjusting valve 405 of the invention is arranged in front of the inlet chamber 422 in terms of flow, and the outlet chamber 423 as well as the first pressure chamber 435 are connected to one another in one piece, as a result of which the sealing seat 14, which is part of the device shown in FIG. 1, and consequently the frictional force at the sealing seat, are eliminated. Thus, the dynamic pressure, which has decreased at the first measuring resistance 406 and is only in the mbar range, prevails in the outlet chamber 423. The pressure in the inlet chamber 422 also decreases due to the throttling action of the anesthetic gas-adjusting valve 405, so that, on the whole, only a markedly weaker resulting pressing force acts on the ball of the ball seat valve 421 compared with the arrangement according to FIG. 1. The space located between the diaphragms 431, 432 is divided into a first chamber 436 and a second chamber 437, wherein the chambers 436, 437 are connected to one another via an annular gap 438. The annular gap 438 is designed as a flow resistance between the chambers 436, 437 and is formed by the difference in diameters between a hole 439 in a projection (projections defining wall portions) 440 within the second proportional element 430 and the slide 433, which is guided by the hole 439. The projection 440 separates the first chamber 436 from the second chamber 437. The first chamber 436 is connected to the environment via a first outlet 441 and a first flow resistance 442, and the second chamber 437 has a corresponding second outlet 443 with a second flow resistance 444.

The axial movement of the slide 433 is damped by the exchange of gas between the chambers 436, 437 via the annular gap 438, on the one hand, and by the exchange of gas between the chambers 436, 437 via the flow resistances 442, 444 with the environment, on the other hand. By adjusting the flow resistances 442, 444 via the annular gap 438, the dynamic behavior of the second proportional valve 430 can be optimized to a new value during the adjusting. The diaphragms 431, 432 are directly connected to the one-piece slide 433 in the second proportional element 430 shown in FIG. 2.

Figure 3:
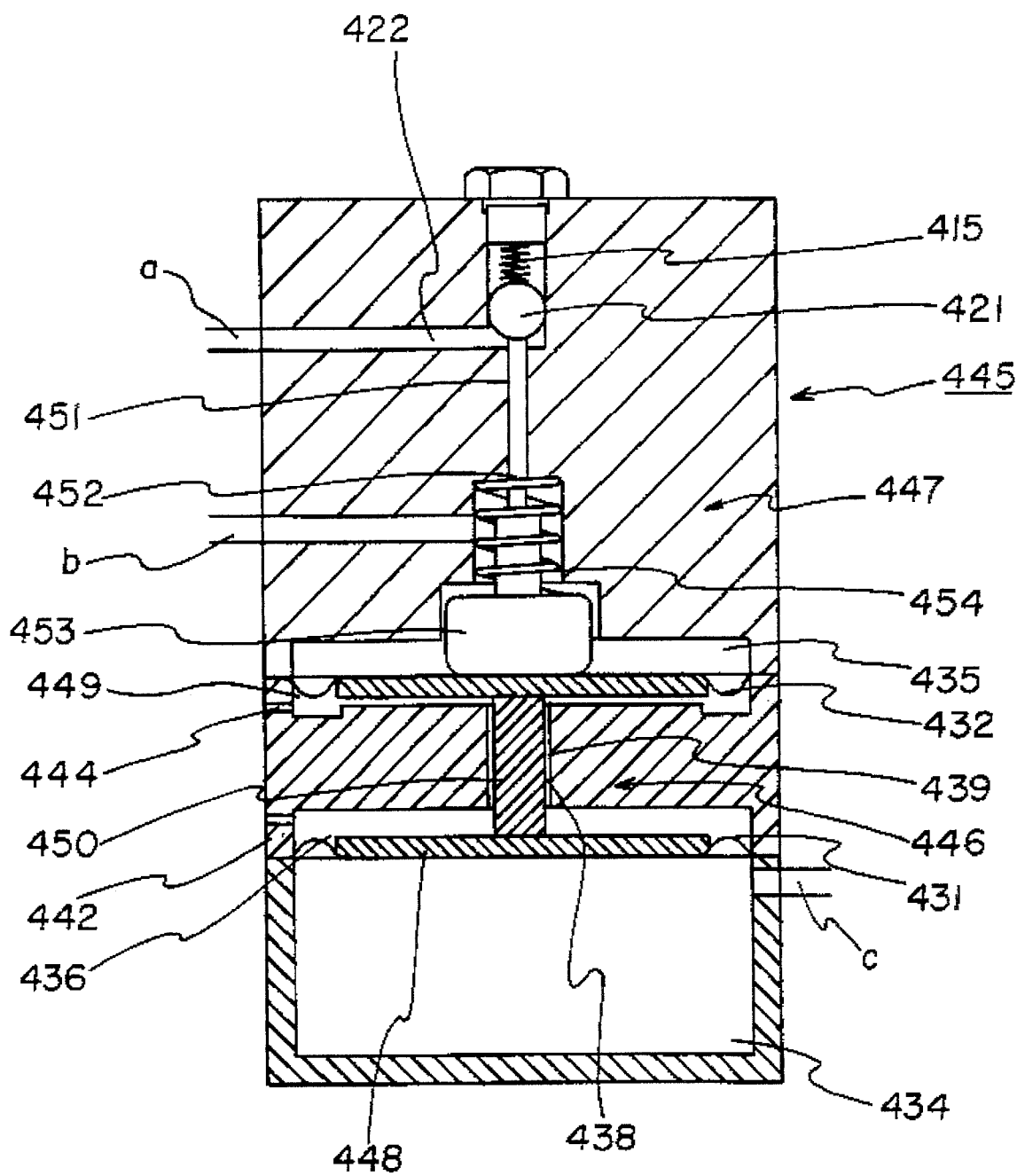
FIG. 3 is a schematic view of a third gas ratio control device according to the present invention.

FIG. 3 shows a third proportional element generally designated 445, which has additional advantageous improvements compared with the second proportional element 430. Identical components are designated by the same reference numbers as in FIG. 2. The difference from FIG. 2 is that the slide 433 is divided into a first slide section 446 and a second slide section 447. The first slide section 446 is comprised of two disk-shaped pressing pieces 448, 449, which are connected to one another by means of a rod 450 guided by a hole 439. The diameter of the hole 439 and that of the rod 450 are selected to be such that the annular gap 438 forming the flow resistance is formed. The diaphragms 431, 432 consist of a flaccid, flexible elastomer, lie flat on the pressing pieces 448, 449, and are displaceable in relation thereto. The second slide section 447 is a plunger 452 which is guided in a clearance fit 451 and has a pressing piece 453 supported by the second diaphragm 432. There is a gas connection between the inlet chamber 422 and the first pressure chamber 435 via the clearance fit 451. The plunger 453 is supported by means of a compression spring 454 in relation to the housing of the third proportional element 445. Frictional forces, especially of the rod 450 within the hole 439, are further reduced by the slide being divided into the first slide section 446 and the second slide section 447, because the diaphragms (431, 432) are displaceable in relation to the pressing pieces 448, 449, as a result of which no mechanical warping can occur between the pressing pieces 448, 449 and the diaphragms 431, 432. In addition, assembly is substantially simplified, because the slide no longer needs to be mechanically connected to the diaphragms 431, 432, unlike in FIGS. 1 and 2. The third proportional element 445 has connections (a, b, c), which are connected to the corresponding lines (a,b,c) of the connection diagram in FIG. 2.

What is claimed is:

1. A gas control device for anesthesia apparatus, comprising:

an anesthetic gas feed line which includes in a series connected arrangement, a control valve with an inlet chamber and an outlet chamber, an anesthetic gas adjusting valve, and a first measuring resistance;

an oxygen feed line which has, in a series connected arrangement, an oxygen adjusting valve, a second measuring resistance, a proportional element with a first chamber including a first pressure chamber which receives dynamic pressure from said first measuring resistance and a remainder of said first chamber, said first pressure chamber being limited by a first diaphragm and a second chamber including a second pressure chamber which receives dynamic pressure from said second measuring resistance and a remainder of said second chamber, said second pressure chamber being limited by a second diaphragm;

a slide connecting said diaphragms, said slide being connected to said control valve, said first diaphragm separating said first pressure chamber from said remainder of said first chamber and said second diaphragm separating said second pressure chamber from said remainder of said second chamber, said slide extending through said remainder of said first chamber and extending through said remainder of said second chamber, said first chamber and said second chamber being divided by a projection, said remainder of said first chamber and said remainder of said second chamber having volumes influenced by the deflection of said first diaphragm and said second diaphragm respectively, said outlet chamber and said first pressure chamber being in fluid communication with one another, said anesthetic gas adjusting valve being arranged in front of said inlet chamber, with regard to a direction of flow, said projection defining a flow resistance throttling an exchange of gas between said remainder of said first chamber and said remainder of said second chamber remainder.

2. A gas ratio control device according to claim 1, wherein said remainder of said first chamber and said remainder of said second chamber each include an outlet and a flow resistance element, said outlet leading via said flow resistance element to the environment.

3. A gas ratio control device according to claim 1, wherein said projection includes a cylindrical hole accommodating said slide, said flow resistance element being formed by an annular gap between an interior surface of said hole and said slide.

4. A gas ratio control device according to claim 3, wherein said slide comprises a first slide section and a second slide section, said first slide section including pressing pieces in contact with said diaphragm and a cylindrical rod which connects said pressing pieces, said cylindrical rod being guided in said hole, said annular gap being defined between an interior surface of said hole and said rod, said second slide section including means for actuating said control valve in the form of a spring-loaded plunger displaceable within a plunger clearance region.

5. A gas ratio control device according to claim 4, wherein said diaphragms are formed of a flaccid, flexible elastomer.

* * * * *

UNITED STATES PATENT AND TRADEMARK OFFICE
CERTIFICATE OF CORRECTION

PATENT NO. : 5,537,993
DATED : July 23, 1996
INVENTOR(S) : REICHERT et al.

It is certified that error appears in the above-indentified patent and that said Letters Patent is hereby corrected as shown below:

On the title page, Item [54] and col. 1, lines 1-2, should read:

--GAS RATIO CONTROL DEVICE FOR ANESTHESIA APPARATUS--

Signed and Sealed this

Twelfth Day of November, 1996

Attest:

BRUCE LEHMAN

*Attesting Officer*    *Commissioner of Patents and Trademarks*